(12) United States Patent
Ostroff

(10) Patent No.: US 7,062,329 B2
(45) Date of Patent: Jun. 13, 2006

(54) IMPLANTABLE CARDIAC SYSTEM WITH A SELECTABLE ACTIVE HOUSING

(75) Inventor: Alan H. Ostroff, San Clemente, CA (US)

(73) Assignee: Cameron Health, Inc., San Clemente, CA (US)

(*) Notice: Subject to any disclaimer, the term of this patent is extended or adjusted under 35 U.S.C. 154(b) by 614 days.

(21) Appl. No.: 10/265,005

(22) Filed: Oct. 4, 2002

(65) Prior Publication Data

US 2004/0068303 A1  Apr. 8, 2004

(51) Int. Cl.
*A61N 1/04* (2006.01)
(52) U.S. Cl. .................. 607/37; 607/36; 607/116; 607/199; 607/122
(58) Field of Classification Search ............... 607/122, 607/36, 37, 27, 116, 119
See application file for complete search history.

(56) References Cited

U.S. PATENT DOCUMENTS

| | | | |
|---|---|---|---|
| 4,157,720 A | 6/1979 | Greatbatch | |
| 4,223,678 A | 9/1980 | Langer et al. | |
| 4,407,288 A | 10/1983 | Langer et al. | |
| 4,628,934 A * | 12/1986 | Pohndorf et al. | 607/27 |
| 4,800,883 A | 1/1989 | Winstrom | |
| 4,830,005 A | 5/1989 | Woskow | |
| 5,095,902 A * | 3/1992 | Ljungstroem | 607/37 |
| 5,129,392 A | 7/1992 | Bardy et al. | |
| 5,133,353 A | 7/1992 | Hauser | |
| 5,184,616 A | 2/1993 | Weiss | |
| 5,203,348 A | 4/1993 | Dahl et al. | |
| 5,230,337 A | 7/1993 | Dahl et al. | |
| 5,261,400 A | 11/1993 | Bardy | |
| 5,300,106 A | 4/1994 | Dahl et al. | |
| 5,330,522 A * | 7/1994 | Kreyenhagen | 607/122 |
| 5,331,966 A | 7/1994 | Bennett et al. | |
| 5,366,496 A | 11/1994 | Dahl et al. | |
| 5,376,103 A | 12/1994 | Anderson et al. | |

(Continued)

FOREIGN PATENT DOCUMENTS

EP  0 517 494 A3  12/1992

(Continued)

OTHER PUBLICATIONS

International Search Report dated Mar. 26, 2002, PCT/US01/29168 filed Sep. 14, 2001, published as WO 02/22208 on Mar. 21, 2002, Subcutaneous Only Implantable Cardioverter Defibrlillator & Optional Pacer, Inventors: Gust H Bardy et al.

(Continued)

*Primary Examiner*—Carl Layno
*Assistant Examiner*—Shevon Johnson
(74) *Attorney, Agent, or Firm*—Crompton, Seager & Tufte, LLC

(57) ABSTRACT

The housing of an implantable cardiac device is selectively made active or passive by an external connector member, such as a shorting plug or lead connector inserted in its header. Advantageously, the header, the shorting plug, and the lead connector all are constructed and arranged to conform to a pre-selected standard in the industry, such as IS-4. The header includes an access hole that is provided with several housing connector elements connected either to the conductive surface or to an internal electrical circuit. The external connector members each have a shaft with external conductor elements. Each shaft includes conductors such as wires. The housing is made active by inserting into the header an external connector element having two of its external connector elements connected by a shorting wire.

18 Claims, 3 Drawing Sheets

U.S. PATENT DOCUMENTS

| | | | |
|---|---|---|---|
| 5,385,574 | A | 1/1995 | Hauser et al. |
| 5,411,539 | A | 5/1995 | Neisz |
| 5,466,253 | A * | 11/1995 | Doan .................... 607/122 |
| 5,507,781 | A | 4/1996 | Kroll et al. |
| 5,531,766 | A | 7/1996 | Kroll et al. |
| 5,534,019 | A | 7/1996 | Paspa |
| 5,545,189 | A | 8/1996 | Fayram |
| 5,603,732 | A | 2/1997 | Dahl et al. |
| 5,620,477 | A | 4/1997 | Pless et al. |
| 5,843,132 | A | 12/1998 | Ilvento |
| 5,899,930 | A | 5/1999 | Flynn et al. |
| 5,906,634 | A | 5/1999 | Flynn et al. |
| 6,058,328 | A | 5/2000 | Levine et al. |
| 6,093,173 | A | 7/2000 | Balceta et al. |
| 6,144,879 | A | 11/2000 | Gray |
| 6,167,314 | A | 12/2000 | Fischer et al. |
| 6,208,900 | B1 | 3/2001 | Ecker et al. |
| 6,241,751 | B1 | 6/2001 | Morgan et al. |
| 6,266,567 | B1 | 7/2001 | Ishikawa et al. |
| 6,280,462 | B1 | 8/2001 | Hauser et al. |
| 6,330,477 | B1 | 12/2001 | Casavant |
| 6,895,276 | B1 * | 5/2005 | Kast et al. .................... 607/37 |

FOREIGN PATENT DOCUMENTS

| | | |
|---|---|---|
| EP | 0 517 494 B1 | 12/1992 |
| EP | 0 627 237 A1 | 12/1994 |
| WO | WO 97/29802 A2 | 8/1997 |
| WO | WO 99/53991 A1 | 10/1999 |

OTHER PUBLICATIONS

Written Opinion dated Sep. 10, 2002, PCT/US01/29168 filed Sep. 14, 2001, published as WO 02/22208 on Mar. 21, 2002, Subcutaneous Only Implantable Cardioverter Defibrlillator & Optional Pacer. Inventors: Gust H Bardy et al.

International Search Report dated Mar. 21, 2002,, PCT/US01/29106 filed Sep. 14, 2001, published as WO 02/24275 on Mar. 28, 2002, Unitary Subcutaneous Only Implantable Cardioverter Defibrillator & Optional Pacer, Inventors: Gust H Bardy et al.

Written Opinion dated Sep. 3, 2002, PCT/US01/29106 filed Sep. 14, 2001, published as WO 02/24275 on Mar. 28, 2002, Unitary Subcutaneous Only Implantable Cardioverter Defibrillator & Optional Pacer Inventors: Gust H Bardy et al.

Journal of the American Medical Association (JAMA), vol. 214, No. 6, 1123pp, Nov. 9, 1970, "Completely Implanted Defibrillator", an editorial comment by JC Schuder PhD.

Amer Soc Trans Artif Int Organs, vol. XVI, 1970, 207-212pp, "Experimental Ventricular Defibrillation With An Automatic & Completely Implanted System", by JC Schuder PhD et al.

Archives of Internal Medicine (Specialized Journal of the AMA), vol. 127, Feb. 1971, Letters to the Editor 317pp, "Standby Implanted Defibrillators", an editirial comment by JC Schuder PhD.

Journal of the American Medical Association (JAMA), vol. 213, 615-616pp, 1970, "Automatic Detection & Defibrillation of Lethal Arrhythmias—A New Concept", by Mirkowski et al.

IEEE Transactions on Bio-Medical Engineering, vol. BME-18, No. 6, Nov. 1971, 410-415pp, "Transthoracic Ventricular Defibrillation In The Dog With Truncated and Untruncated Exponential Stimuli" by JC Schuder PhD et al.

Pace, vol. 16, Part I, Jan. 1993, 95-124pp, "The Role Of An Engineering Oriented Medical Research Group In Developing Improved Methods & Devices For Achieving Ventricular Defibrillation: The University Of Missouri Experience", by JC Schuder PhD.

Journal of Cardiovascular Electrophysiology, vol. 12, No. 3, Mar. 2001, 356-360pp, Copyright 2001, by Future Publishing Company Inc, Armonk-NY 1050-0418, "Nonthoracotomy Implantable Cardioverter Defibrillator Placement In Children", by Rainer Gradaus MD et al.

Journal of Cardiovascular Electrophysiology, vol. 12, No. 3, Mar. 2001, 361-362pp, Copyright 2001, by Future Publishing Company Inc, Armonk-NY 1050-0418, "Implantable Defibrillators In Children: From Whence to Shock" by Richard A Friedman MD et al.

* cited by examiner

IMPLANTABLE CARDIAC SYSTEM WITH A SELECTABLE ACTIVE HOUSING

BACKGROUND OF THE INVENTION

1. Field of Invention

This invention pertains to a cardiac system with an implantable housing that can be selectively rendered to be active or passive. More particularly, the invention describes a cardiac system including housing with a header, a plug and/or a connector with a lead terminating with one or more electrodes and adapted to be inserted into the housing. The structure of the plug or connector defines whether the housing is active or passive.

2. Description of the Prior Art

Implantable cardiac devices are used extensively to provide therapy to patients with various cardiac problems. The therapy from these types of devices usually consists of the application of electrical stimulation pulses to cardiac tissues. Typically, each such device typically consists of sensing circuitry used to sense intrinsic cardiac signals, generating circuitry used to generate electrical stimulation signals, control circuitry used to control the operation of the device, and various auxiliary circuitry used to perform other functions, such as telemetry, data logging, etc. This circuitry is contained in a housing suitable for implantation. The housing further includes a header used to connect the circuitry contained in the housing to one or more leads which extend into, or at least in the vicinity of, the patient's heart and terminate in one or more electrodes. Various header structures are disclosed in U.S. Pat. Nos. 5,545,189; 5,620,477; 5,899,930; 5,906,634; 6,167,314; 6,208,900; and 6,330,477, all incorporated herein by reference.

At least two electrodes are required for sensing, stimulation and some other functions of the device. In many instances, for example, when the housing is implanted pectorally, it is advantageous to have the housing act as one of the electrodes. In these instances, typically at least a portion of the housing's outer surface is exposed and is composed of a conductive material. This portion is then electrically connected to the circuitry within the housing and plays an active part in the operation of the circuitry (i.e., is used to provide stimulation, sensing and/or other functions). Such a housing is often referred to as an 'active' housing.

However, an active housing may not be desirable for all locations (e.g., abdominal) because it may be too distant from the heart to be effective, or because it may be, in some instances, adjacent to a muscle that is adversely affected by electrical stimulation.

A housing could be constructed from the start as an active or passive housing by providing an appropriate electrical link between the housing surface and its circuitry. However, this approach is impractical if the decision as to which kind of housing to use is made at the last minute, i.e., just prior to implantation. Since most cardiac devices are programmable, an electrically controlled switch could be used as the link and the decision as to whether to make a housing active or not could be another programming parameter. However, such electrically controlled switches use up space within the housing and add cost and complexity to the electrical circuitry.

U.S. Pat. No. 5,620,477 discloses a housing 12 that can be rendered selectively active and passive using a mechanical element. This housing makes use of a special header having two connector blocks 34, 36. Connector block 34 is connected to an internal circuit while connector block 36 is connected to the conductive surface 16. The housing 12 is rendered active by a plug inserted into the header and having a long connector pin 54 which is positively attached to the connector blocks 34, 36, thereby effectively shorting the two connector blocks to each other. Alternatively, a lead connector is provided with its own connector pin 54. The problem with this approach is that it requires a special design for both the housing header and the plug or lead connector. Thus, this housing cannot be used with standard multi-lead connectors conforming to specific standards, such as an IS-4 quadripolar lead connector.

SUMMARY OF THE INVENTION

The present invention provides a novel implantable cardiac housing that overcomes the deficiencies of such existing housings. More particularly, an implantable cardiac device is disclosed having a housing with a header. The header is structured to accept an external connector member such as a plug or a multiple conductor lead connector conforming to a pre-selected standard such as IS-4. The header includes a plurality of housing connector elements that come into contact with the external connector member. One of these housing connector elements is connected to a conductive portion of the housing. Another of the housing connector elements is connected to an internal electrical circuit disposed within the housing.

Each of the external connector members has a shaft with a plurality of external connector elements. The external connector elements are wired in a manner that connects distant electrodes to the internal electrical circuit. In addition, in certain embodiments of the present invention, the external connecting elements include a shorting wire to connect two housing connector elements, thereby rendering the housing active. Alternatively, If the housing is to remain passive, no shorting wire is provided.

DETAILED DESCRIPTION OF THE INVENTION

Figure 1:
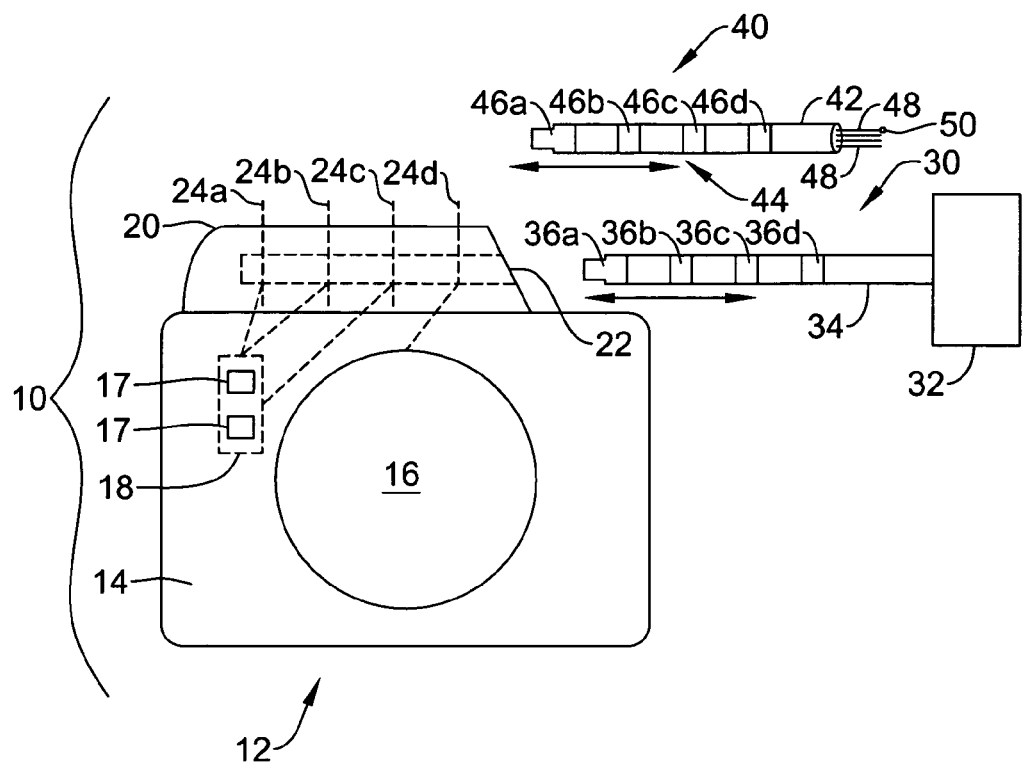
FIG. 1 shows a side view of the housing of a cardiac device and a shorting plug constructed in accordance to this invention.

Referring now to the drawings, a cardiac system 10 constructed in accordance with this invention includes a housing 12 with an external surface 14. A portion 16 of the external surface 14 is made of an electrically conductive material, such as stainless steel, a titanium alloy, or other electrically conductive materials known in the art. Alternatively, the entire surface of the housing 10 could be made conductive. The housing 12 holds a power supply (not shown) and various electrical circuits 17 used to sense intrinsic cardiac signals, generate stimulation pulses and perform other similar conventional functions. These electrical circuits are provided on one or more circuit boards 18.

The housing 12 is hermetically sealed and includes a header 20 made of an epoxy or other similar non-conductive material.

The header 20 is formed with one or more access holes 22 to provide a means of interfacing the housing 12 with one or more external connector members. Examples of external connector members include a shorting plug 30 and a lead connector 40. Furthermore, the header 20 is formed to enable these external connector members to be electrically coupled to the circuits contained within the housing 12.

Each access hole 22 may be used to provide one or more connections. More particularly, several housing connector elements 24A, 24B, 24C, 24D are disposed axially along the access hole 22. These housing connector elements may comprise contacting blades, springs, screws or any other similar conventional connecting mechanisms known in the art. Housing connector elements 24A, 24B, 24C are electrically coupled to one of the circuits 17 on board 18. Housing connector element 24D is electrically coupled to the conductive portion 16 of the housing 12.

The header 20 is arranged and constructed to electrically couple the external connector members (such as a shorting plug 30 or a lead connector 40 for a multi-electrode lead) to the electrical circuits 17 when the external connector members are inserted into the access hole 22.

The shorting plug 30 includes a head 32 and a shaft 34. The head 32 portion of the shorting plug 30 is used to hold and manipulate the shorting plug 30 during its insertion into the access hole 22. The shaft 34 portion of the shorting plug 30 is constructed in accordance with standard guidelines set for multi-electrode connectors, such as IS-4.

The external connector elements 36A, 36B, 36C, 36D are disposed about the shaft 34 of the shorting plug 30. In the configuration shown in FIG. 1, the connecting element 36A forms the tip of the shaft 34, while the connector elements 36B, 36C, 36D are ring-shaped and are axially spaced from the shaft tip. The external connector elements 36A–36D are formed of a conductive biocompatible material. The regions between the connector elements on the shaft 34, however, are made of an insulating or non-conductive material.

When the shaft of the external connecting member (in this case, the shorting plug 30) is properly positioned within the access hole 22, the external connector elements 36A–36D couple to the housing connector element 24A–24D located within the header 20. This subsequent union provides an electrical connection between the external connector member and the cardiac system 10.

The lead connector 40 similarly has a proximal end consisting of a shaft 44. Disposed along the proximal end of the shaft 44 are external connector elements 46A, 46B, 46C, 46D. External connector elements 46A–46D are constructed and function to the external connector elements 36A–36D described with reference to the shorting plug 30. Lead connector 40 is attached to a lead 42 which includes a plurality of conductors 48. The plurality of conductors 48 terminate and are connected distally to an electrode 50. Proximally, the plurality of conductors 48 are connected to one of the external connector elements 46A–46D.

In one embodiment, the lead 42 is implanted with the electrodes 50 disposed in the patient's cardiac chambers. In an alternative embodiment, the lead is implanted with the electrodes 50 disposed subcutaneously within the patient's anatomy. Similarly, particular embodiments of the present invention include a combination of electrodes 50 disposed subcutaneously around the patient's thorax and transvenously within the patient's heart.

Figure 2:
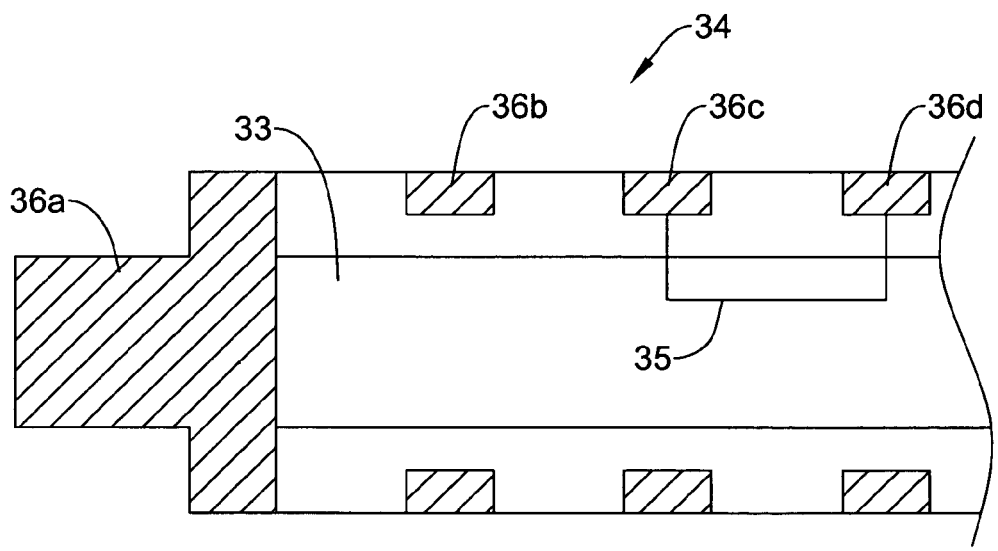
FIG. 2 shows a partial cross-sectional of the shorting plug of FIG. 1.

FIG. 2 shows a cross-sectional partial view of the shaft of an external connecting member. In particular, FIG. 2 depicts a portion of the shaft 34 of the shorting plug 30. The shaft portion of the external connecting members is constructed to permit connections between external connector elements. For example, as depicted in FIG. 2, a shorting element 35 may be provided between external connector elements 36C and 36D. This design flexibility, in particular the electrical interactions between external connector elements, permits external connecting members to be used in mechanically programming a cardiac system 10 to have a housing that is active or passive.

In illustration, when the shorting plug 30 is fully inserted into the access hole 22, the external connector elements 36A–36D come into electrical contact with the respective housing connector elements 24A–24D contained within the access hole 22. If the housing connector elements 24C and 24D are coupled to the circuit board 18 and to the conductive portion 16 of the housing 12 respectively, when the shorting plug 30 depicted in FIG. 2 is inserted into the access hole 22, the conductive portion 16 of the housing 12 is connected to the board 18, thereby rendering the housing 12 active.

External connecting members may be used to mechanically program a cardiac system 10 having a single access hole 22, or alternatively, having multiple access holes. When the cardiac system 10 possesses a single access hole 22, a lead connector 40 is utilized to mechanically program the cardiac system 10 as active or passive. Alternatively, when the cardiac system includes multiple access holes 22, a combination of shorting plugs 30 and lead connectors 40 can be utilized to mechanically program the cardiac system 10 to a desired configuration.

In a cardiac system 10 having two access holes 22, there are at least five different combinations in which to arrange the external connecting members to mechanically program the cardiac system 10 as active or passive. One grouping of combinations utilizes two lead connectors 40. In this grouping, both lead connectors 40 may be constructed to mechanically render the cardiac system 10 passive. Alternatively, one lead connector 40 may be constructed to render a passive cardiac system 10, whereas the second lead connector 40 may be constructed for rendering the cardiac system 10 active. The result of such a lead connector 40 arrangement would be an active cardiac system 10 having two distally positioned electrodes.

A second grouping utilizes a single lead connector 40 and a single shorting plug 30. In this grouping, both lead external connecting members may be constructed for mechanically rendering a passive cardiac system 10. Alternatively, the lead connector 40 may be constructed for rendering the cardiac system 10 passive, whereas the shorting plug 30 may be constructed to render the cardiac system 10 active. Another conceivable arrangement is to have the lead connector 40 render the cardiac system 10 active and the shorting plug 30 render the cardiac system 10 passive. Again, in either of the last two examples, the result of such external connecting member arrangements would be an active cardiac system 10 having a distally positioned electrode.

FIGS. 2–5 further illustrate how within a single external connecting member, the interactions between external connecting elements may be configured to provide an array of mechanical programming for the cardiac system 10.

Figure 3:
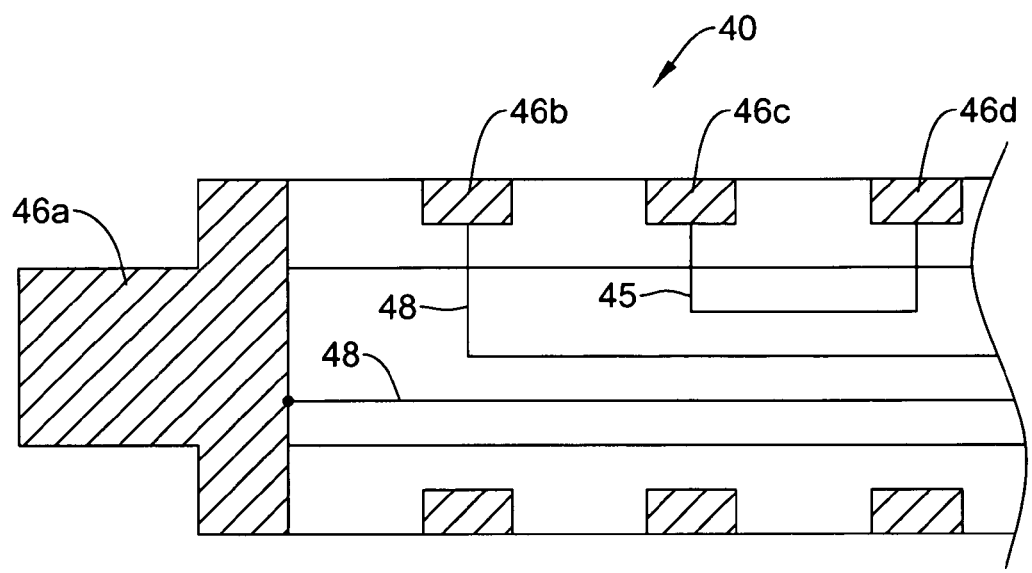
FIG. 3 shows a partial cross-sectional view of a first lead connector similar to the connector of the shorting plug of FIG. 2.

FIG. 3 shows the structure of the lead connection 40 if the housing 12 is to be an active housing. As shown in this Figure, conductors 48 are attached to external connector elements 46A, 46B and a shorting wire 45 is provided between external connector elements 46C and 46D. In this manner, the circuit board 18 is connected to the housing portion 16.

Figure 4:
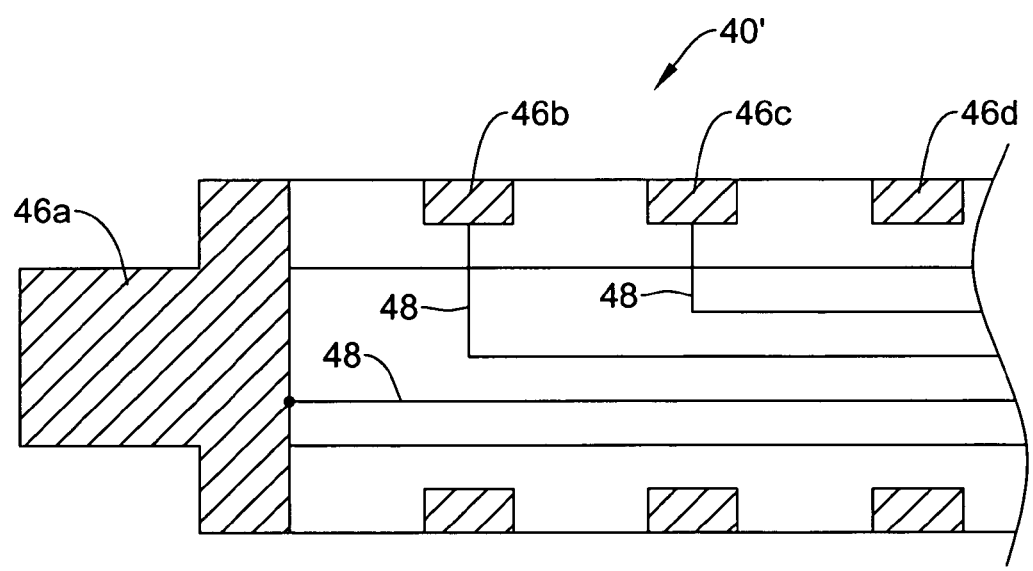
FIG. 4 shows a partial cross-sectional view of a second lead connector used for an passive housing.

FIG. 4 shows alternative construction for a lead connection 40. As seen in this Figure, the external connector elements 46A, 46B, 46C are all connected to a respective conductor 48 while the external connection element 46D is not connected to a conductor 48. As a result, when the lead connector 40' is inserted into the housing 12, the housing 12 is passive.

Figure 5:
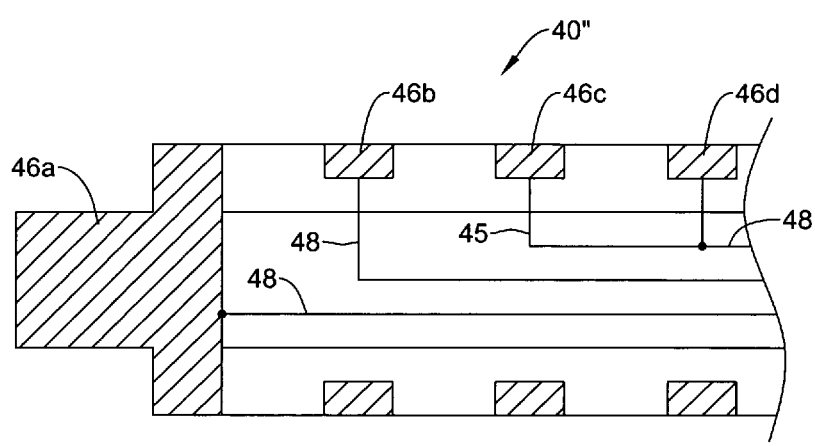
FIG. 5 shows a partial cross-sectional view of a third lead connector in which the housing is active and is electrically connected to a remote electrode.

FIG. 5 shows yet another alternate construction for a lead connector 40". In this embodiment the external connector elements 46C, 46D are connected to each other by a wire 45 and to a conductor 48. This arrangement may be advantageous if multiple current paths are desired.

While the invention has been described with reference to several particular embodiments, it is to be understood that these embodiments are merely illustrative of the principles of the invention. Accordingly, the embodiments described in particular should be considered as exemplary, not limiting, with respect to the following claims.

I claim:

1. An implantable cardiac system comprising: a housing holding an electrical circuit and having a conductive surface and a header, the header being formed with an access hole and a plurality of housing connector elements arranged in the access hole that selectively couple to the conductive surface and the electrical circuit; and an external connector member adapted to be inserted into the access hole, the external connector member being formed with a plurality of external connector elements being arranged and constructed to mechanically and electrically contact the housing connector elements when the external connector member is inserted into the access hole, wherein the external connector member includes at least one electrical interconnection between the first external connector element and the second external connector element that, when the external connector member is inserted into the housing, causes the housing to become an active housing.

2. The implantable cardiac system of claim 1, wherein the external connector member includes a shaft having the external connector elements spaced axially along the shaft.

3. The implantable cardiac system of claim 1, wherein the at least one electrical interconnection mechanically programs the cardiac system for an active housing.

4. The implantable cardiac system of claim 1, wherein the header further includes a first housing connector element coupled to the conductive surface and a second housing connector element coupled to the electrical circuit.

5. The implantable cardiac system of claim 1, wherein the external connector member is a shorting plug.

6. The implantable cardiac system of claim 1, wherein the external connector member is a lead connector.

7. An implantable cardiac system comprising:

a housing comprising a conductive outer surface, a header, and an electrical circuit disposed within the housing, wherein the header further includes at least two access holes extending through the header and having a plurality of housing connector elements spaced axially along each of the access holes, wherein the housing connector elements are selectively connected to the conductive outer surface of the housing and the electrical circuit;

a lead connector sized and shaped to fit into one access hole and having a plurality of external connector elements being spaced axially along a proximal portion of the lead connector that mechanically and electrically couple to the plurality of housing connector elements; and an external connector member sized and shaped to fit into a second access hole and having a plurality of external connector elements along a proximal portion of the external connector member that mechanically and electrically couples to the plurality of housing connector elements;

wherein at least one of the external connector member and the lead connector includes first and second external connector elements with an electrical interconnection therebetween, such that, when inserted to a corresponding access hole, the electrical interconnection between the first and second external connector elements renders the housing active.

8. The implantable cardiac system of claim 7, wherein the external connector member is a second lead connector.

9. The implantable cardiac system of claim 8, wherein the first lead connector renders the cardiac system passive and the second lead connector renders the cardiac system passive.

10. The implantable cardiac system of claim 8, wherein the first lead connector renders the cardiac system passive and the second lead connector renders the cardiac system active.

11. The implantable cardiac system of claim 7, wherein the external connector member is a shorting plug.

12. The implantable cardiac system of claim 11, wherein the lead connector renders the cardiac system passive and the shorting plug renders the cardiac system passive.

13. The implantable cardiac system of claim 11, wherein the lead connector renders the cardiac system active and the shorting plug renders the cardiac system passive.

14. The implantable cardiac system of claim 11, wherein the lead connector renders the cardiac system passive and the shorting plug renders the cardiac system active.

15. An implantable cardiac system comprising:

a housing holding an electrical circuit and having a conductive surface and a header, the header being formed with an access hole and a plurality of housing connector elements spaced axially along the access hole and including a first housing connector element connected electrically to the conductive outer surface and a second connector element connected electrically to the electrical circuit; and a shorting plug including a shaft sized and shaped to fit into the access hole, and having a plurality of external connector elements being spaced axially along the shaft, the shorting plug further including a shorting element adapted to electrically short between the first connector element and the second connector element;

wherein the shorting plug and header are sized and shaped to provide electrical contact between each of the external connector elements and the corresponding housing connector element when the shorting plug is inserted into the access hole.

16. The implantable cardiac system of claim 15, wherein the shorting plug includes several external connector elements including a ring disposed circumferentially about the shaft.

17. The implantable cardiac system of claim 15, wherein the shaft has a tip and one of said external connector elements is disposed at the tip.

18. An implantable cardiac system comprising: a housing containing operational circuitry for providing electrical cardiac stimulus, the housing having a conductive surface over a portion thereof and an access hole for receiving a header of a lead for use therewith, the housing also includes a plurality of housing connector elements; and a set of leads for use with the housing and operational circuitry, the set including: a first lead having a proximal end sized for insertion into the access hole; a second lead having a proximal end sized for insertion into the access hole; wherein; the first lead and the second lead each include a plurality of external connector elements adapted to couple with the housing connector elements; wherein: if the first lead is inserted into the housing, the housing is an active-canister type of housing; if the second lead is inserted into the housing, the housing is a passive-canister type of housing; and the first lead includes an electrical interconnection between the first and second external connector elements.

* * * * *